United States Patent
Wuts

(12)
(10) Patent No.: US 6,509,491 B2
(45) Date of Patent: Jan. 21, 2003

(54) AMINOHYDROXYLATION OF OLEFINS IN THE PRESENCE OF ACETAMIDE

(75) Inventor: Peter Guillaume Marie Wuts, Mattawan, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/795,879

(22) Filed: Feb. 28, 2001

(65) Prior Publication Data

US 2001/0029306 A1 Oct. 11, 2001

Related U.S. Application Data

(60) Provisional application No. 60/186,523, filed on Mar. 2, 2000.

(51) Int. Cl.$^7$ ............................................. C07C 229/00
(52) U.S. Cl. ........................................................ 560/41
(58) Field of Search .......................... 560/19, 37, 39, 560/41

(56) References Cited

U.S. PATENT DOCUMENTS 4,871,855 A 10/1989 Marko et al. ................ 546/134
5,767,304 A 6/1998 Sharpless et al. ............. 560/27

FOREIGN PATENT DOCUMENTS

WO        WO 98/27051        6/1998        ......... C07C/231/00

OTHER PUBLICATIONS

Choong Eui Song et al, "One–step synthesis of paclitaxel side–chain precursor: benzamide–based asymmetric aminohydoxylation of isopropyl trans–cinnamate", Tet. Asym., vol. 10 (1999), pp. 671–674.*

G. L. Han–Ting Chang, K. B. Sharpless, "*Catalytic Asymmetric Aminohydroxylation (AA) of Olefins*," Angewandte Chem. International Edition, 1996, 35:4:451–454.

M. Bruncko, G. Schlingloff, K B. Sharpless, "*N. Bromoacetamide—A New Nitrogen Source For the Catalytic Asymmetric Aminohydroxylation of Olefins*," Angewandte Chem. International Edition, 1997, 36:13/14:1483–1486.

\* cited by examiner

*Primary Examiner*—Paul J. Killos
(74) *Attorney, Agent, or Firm*—Bruce Stein

(57) ABSTRACT

The present invention is a process to prepare on of a phenylisoserine ester of the formula (II)

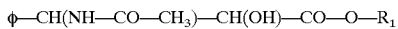

with reduced amount of diol by-product by the use of a compound of the formula $R_2$—CO—$NH_2$ where $R_2$ is $C_1$–$C_6$ alkyl with the proviso that $R_2$ is not tertiary.

19 Claims, No Drawings

AMINOHYDROXYLATION OF OLEFINS IN THE PRESENCE OF ACETAMIDE

CROSS-REFERENCE TO RELATED APPLICATIONS

This application claims the benefit of the following provisional application: U.S. Ser. No. 60/186,523, filed Mar. 2, 2000, under 35 USC 119(e)(i).

BACKGROUND OF THE INVENTION

1. Field of the Invention

The invention is the osmium catalyzed enantiomeric specific aminohydroxylation of olefins in the presence of amides which permits the use of much higher substrate levels.

2. Description of the Related Art

U.S. Pat. No. 5,767,304 discloses a process for the catalytic asymmetric aminohydoxylation of olefins with carbamates.

Angew. Chem. Int. Ed. Engl. 36(13/14), 1483 (1997) discloses a one step process for the metal-catalyzed asymmetric aminohydroxylation of olefins using catalytic amounts of osmium (VIII) and cinchona alkaloid derivatives using N-bromoacetamide as the nitrogen source. This process requires 60 mL of solvent per gram of substrate or if run more concentrated an undesirable diol by-product is produced. The present process permits much higher substrate concentrations with reduced diol by-product formation.

SUMMARY OF INVENTION

Disclosed is a process for the preparation of a phenylisoserine ester of the formula (II)

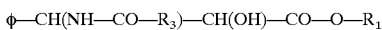

where $R_1$ is $C_1-C_5$ alkyl with the proviso that $R_1$ is not tertiary, where $R_3$ is —$CH_3$ or —$CH_2$—$CH_3$ and the stereochemistry at C-2 is R and at C-3 is S, which comprises:

(1) contacting a mixture of a cinnamate of the formula (I)

where the double bond is in the trans configuration and $R_1$ is as defined above, osmium in one of its oxidation states, cinchona alkaloid or derivative thereof, N-bromoacetamide, N-bromopropionamide, a non-nitrogen base, water, a solvent in which the cinnamate is at least partially soluble, in the presence of a compound of the formula $R_2$—CO—$NH_2$ where $R_2$ is $C_1-C_6$ alkyl with the proviso that $R_2$ is not tertiary.

DETAILED DESCRIPTION OF THE INVENTION

The present invention is a process for the preparation of a compound of the formula (II)

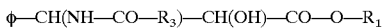

where $R_1$ is $C_1-C_5$ alkyl with the proviso that $R_1$ is not tertiary, where $R_3$ is —$CH_3$ or —$CH_2$—$CH_3$ and the stereochemistry at C-2 is R and at C-3 is S, which comprises:

(1) contacting a mixture of a cinnamate of the formula (I)

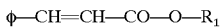

where the double bond is in the trans configuration and $R_1$ is as defined above, osmium in one of its oxidation states, cinchona alkaloid or derivative thereof, N-bromoacetamide or N-bromopropionamide, a non-nitrogen base, water, a solvent in which the cinnamate is at least partially soluble, in the presence of a compound of the formula $R_2$—CO—$NH_2$ where $R_2$ is $C_1-C_6$ alkyl with the proviso that $R_2$ is not tertiary.

The starting material, the trans cinnamate (I), φ—CH=CH—CO—O—$R_1$, is well known to those skilled in the art.

The various reactants of the reaction can be combined in virtually any manner. There is no one specific order of addition that is required.

The osmium can be added in any oxidation state (VI or VIII) and as osmium tetroxide or potassium osmate (potassium osmate dihydrate). The amount of osmium required is catalytic as is known to those skilled in the art.

Cinchona alkaloids are known to those skilled in the art, see Angew. Chem. Int. Ed. Engl. 36(13/14), 1483 (1997), page 1484. The cinchona alkaloid is selected from the group consisting of $(DHQ)_2$-PHAL and $(DHQ)_2$-AQN; it is preferred that the cinchona alkaloid is $(DHQ)_2$-PHAL.

The invention requires an oxidizing agent. It is preferred that the oxidizing agent be N-bromoacetamide or N-bromopropionamide. It is more preferred that the agent be N-bromoacetamide. It is necessary that the N-bromoamide be present in approximately a stoichiometric amount.

The reaction requires a non-nitrogen base. It is preferred that the non-nitrogen base is selected from the group consisting of hydroxide, carbonate, alkoxides where the alkyl group is from 1 thru 5 carbon atoms, butyl lithium and phosphate buffers with pH greater than approximately 9. It is more preferred that the non-nitrogen base is selected from the group consisting of hydroxide, carbonate, methoxide, ethoxide and t-butoxide. It is even more preferred that the non-nitrogen base is hydroxide, it is most preferred that the hydroxide be lithium hydroxide. It is preferred that approximately one equivalent of non-nitrogen base be present in the reaction mixture.

Water is a necessary reactant to dissolve a number of reactants. In addition to water, the reaction requires a solvent to at least partially dissolve the cinnamate (I). Preferred solvents include acetonitrile and $C_1-C_4$ alcohols or mixtures thereof. It is more preferred that the solvent be t-butyl alcohol. The cinnamate (1) need not be completely dissolved.

To be able to produce the phenylisoserine ester (II) in good yield with the desired enantiomeric selectivity and in high concentrations, it is required to perform the process in the presence of a compound of the formula $R_2$—CO—$NH_2$ where $R_2$ is $C_1-C_6$ alkyl with the proviso that $R_2$ is not tertiary. It is preferred that $R_2$ is $C_1$ alkyl (acetamide). The quantity of acetamide is not critical, 0.1 to more than 1 equivalent is operable. It is preferred that the compound of the formula $R_2$—CO—$NH_2$ be present in approximately one equivalent.

It is preferred to perform the reaction in a temperature range of from about −10° to about 30°; more preferably at about 0° to about 4°.

When the reaction is complete (as measured by TLC, HPLC or other common means of reaction monitoring), it is quenched with an agent such as sulfite, preferably sodium or potassium sulfite, more preferably sodium sulfite.

Following work-up by methods well known to those skilled in the art, the desired phenylisoserine ester (II) is obtained.

The phenylisoserine ester (II) is a useful intermediate in the production of taxol. The phenylisoserine ester (II) is then subjected to the series of reactions set forth in CHART B, all of which are well known to those skilled in the art. In addition, the intermediates of CHART B are well known to those skilled in the art. First, acid hydrolysis removes the amide to produce the amino-alcohol which is a known compound, see Angew. *Chem. Int. Ed. Engl.* 36(13/14), 1483 (1997). Second, both the amino and alcohol groups are protected. The amino group is preferably protected/substituted by the substituent, φ-CO—, which is required to be present in taxol itself. Therefore, the φ-CO— group serves a dual purpose, to protect the amino group and to add a substituent which is required in the ultimate end product, taxol. The alcohol group is protected by an alcohol protecting group, $X_1$ which are well known to those skilled in the art and include groups such as, ethoxyethyl ether, t-butyldimethylsilyl ether and dihydropyranyl ether. The third step is hydrolysis of the ester to produce the amino-alcohol protected phenyisoserine acid. The amino-alcohol protected phenylisoserine acid is known to be a useful intermediate in the preparation of taxol see U.S. Pat. No. 4,924,011, formula (III). The first step of CHART B, is usually performed in an alcohol solvent. When the alcohol is other than the alcohol portion of the ester, transesterification takes place. Therefore, if the preferred isopropyl phenylisoerine (II) is contacted with acid in methanol, the resulting deacylated product is the methyl ester, as is known to those skilled in the art.

Definitions and Conventions

The definitions and explanations below are for the terms as used throughout this entire document including both the specification and the claims.

Definitions

All temperatures are in degrees Centigrade.

TLC refers to thin-layer chromatography.

HPLC refers to high pressure liquid chromatography.

Saline refers to an aqueous saturated sodium chloride solution.

NMR refers to nuclear (proton) magnetic resonance spectroscopy, chemical shifts are reported in ppm (δ) downfield from tetramethylsilane.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

DHQ refers to

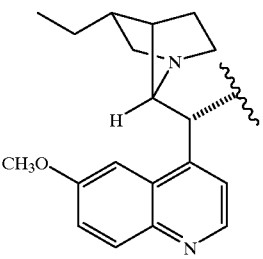

PHAL refers to

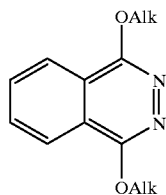

AQN refers to

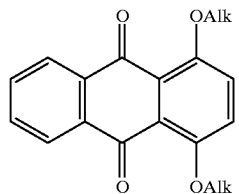

DHQ is the "Alk" portion of PHAL and AQN.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1

Isopropyl (2R,3S)-3-(acetylamino)-2-hydroxy-3-phenylpropanoate (II)

Lithium hydroxide-hydrate (236 mg, 5.63 mmol) and osmium tetroxide (53 mg, 0.210 mmol) are dissolved in a minimal amount of water. To this is added t-butanol (8 ml) and (DHQ)$_2$PHAL (205 mg, 0.263 mmol) and the reaction mixture is stirred for 10 minutes. Water (12 ml) is added and the reaction mixture is cooled in an ice bath to less than 4°. Acetamide (311 mg, 5.26 mmol), isopropyl cinnamate (I, 1.00 g, 5.26 mmol), and N-bromoacetamide (795 mg, 5.63 mmol) respectively are added to the reaction mixture. The mixture is stirred until complete as measured by HPLC. The reaction mixture is quenched with a small amount of sodium sulfite (50 mg) and allowed to warm to 20–25°. Ethyl acetate (5 ml) is added and the reaction mixture is stirred for 30 minutes. The phases are separated and the aqueous layer is extracted three times with ethyl acetate (30 ml). The organic layers are combined and washed three times with saline (30 ml). The organic layer is dried with sodium sulfate and filtered through a small amount of silica. The mixture is concentrated on a rotary evaporator and the product is recrystallized from ethyl acetate/hexane to give the title compound; mp=104–106°; HMR (300 MHz, CDCl$_3$) 1.30, 2.00, 3.20, 4.78, 5.05, 5.55, 6.23 and 7.35 δ.

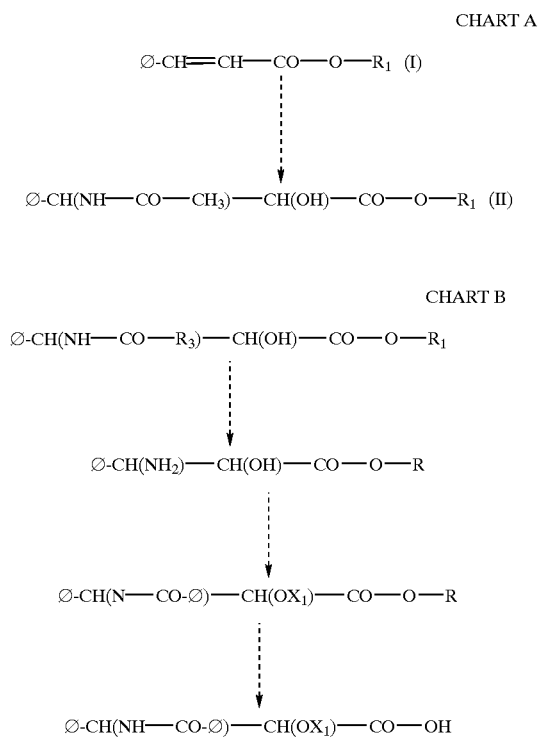

CHART A

∅-CH=CH—CO—O—R$_1$  (I)

↓

∅-CH(NH—CO—CH$_3$)—CH(OH)—CO—O—R$_1$  (II)

CHART B

∅-CH(NH—CO—R$_3$)—CH(OH)—CO—O—R$_1$

↓

∅-CH(NH$_2$)—CH(OH)—CO—O—R

↓

∅-CH(N—CO-∅)—CH(OX$_1$)—CO—O—R

↓

∅-CH(NH—CO-∅)—CH(OX$_1$)—CO—OH

What is claimed is:

1. A process for the preparation of a phenylisoserine ester of the formula (II)

φ—CH(NH—CO—R$_3$)—CH(OH)—CO—O—R$_1$ where R$_1$ is C$_1$–C$_5$ alkyl with the proviso that R$_1$ is not tertiary, where R$_3$ is —CH$_3$ or —CH$_2$—CH$_3$ and the stereochemistry at C-2 is R and at C-3 is S, which comprises:

(1) contacting a mixture of a cinnamate of the formula (I)

φ—CH=CH—CO—O—R$_1$ where the double bond is in the trans configuration and R$_1$ is as defined above, osmium in one of its oxidation states, cinchona alkaloid or derivative thereof, either N-bromoacetamide, or N-bromopropionamide, a non-nitrogen base, water, a solvent in which the cinnamate is at least partially soluble, in the presence of a compound of the formula R$_2$—CO—NH$_2$ where R$_2$ is C$_1$–C$_6$ alkyl with the proviso that R$_2$ is not tertiary.

2. A process according to claim 1 where R$_1$ is i-propyl or i-butyl.

3. A process according to claim 2 where R$_1$ is i-propyl.

4. A process according to claim 1 where the osmium is present in oxidation state (VIII).

5. A process according to claim 1 where the osmium is osmium tetroxide or potassium osmate.

6. A process according to claim 5 where the osmium is osmium tetroxide.

7. A process according to claim 1 where the cinchona alkaloid is selected from the group consisting of (DHQ)$_2$-PHAL and (DHQ)$_2$-AQN.

8. A process according to claim 1 where the cinchona alkaloid is (DHQ)$_2$—PHAL.

9. A process according to claim 1 where the reactant is N-bromoacetamide.

10. A process according to claim 1 where the non-nitrogen base is selected from the group consisting of hydroxide, carbonate, alkoxides where the alkyl group is from 1 thru 5 carbon atoms, butyl lithium and phosphate buffers with pH greater than approximately 9.

11. A process according to claim 10 where the non-nitrogen base is selected from the group consisting of hydroxide, carbonate, methoxide, ethoxide and t-butoxide.

12. A process according to claim 11 where the non-nitrogen base is hydroxide.

13. A process according to claim 12 where the non-nitrogen base is lithium hydroxide.

14. A process according to claim 1 where the solvent is selected from the group consisting of acetonitrile and C$_1$–C$_4$ alcohols.

15. A process according to claim 14 where the solvent is t-butyl alcohol.

16. A process according to claim 1 where R$_2$ is C$_1$ or C$_2$.

17. A process according to claim 1 where R$_2$ is C$_1$.

18. A process according to claim 1 where the compound of the formula R$_2$—CO—NH$_2$ is present in an amount of about 1 equivalent.

19. A process for the preparation of isopropyl (2R,3S)-3-(acetylamino)-2-hydroxy-3-phenylpropanoate of the formula (II)

φ—CH(NH—CO—CH$_3$)—CH(OH)—CO—O—CH(CH$_3$)$_2$ where the stereochemistry at C-2 is R and at C-3 is S, which comprises:

(1) contacting a mixture of a cinnamate of the formula (I)

φ—CH=CH—CO—O—CH(CH$_3$)$_2$ where the double bond is in the trans configuration and osmium tetroxide, (DHQ)$_2$-PHAL, N-bromoacetamide, hydroxide, water and t-butyl alcohol in the presence of acetamide.

* * * * *